(12) United States Patent
Li et al.

(10) Patent No.: US 9,642,577 B1
(45) Date of Patent: May 9, 2017

(54) METHODS AND SYSTEMS FOR DISEASE ANALYSIS BASED ON TRANSFORMATIONS OF DIAGNOSTIC SIGNALS

(71) Applicant: American Reliance, Inc., El Monte, CA (US)

(72) Inventors: Fu Yu Li, Azusa, CA (US); Edward Chen, San Marino, CA (US)

(73) Assignee: American Reliance, Inc., El Monte, CA (US)

( * ) Notice: Subject to any disclaimer, the term of this patent is extended or adjusted under 35 U.S.C. 154(b) by 0 days.

(21) Appl. No.: 15/237,913

(22) Filed: Aug. 16, 2016

(51) Int. Cl.
*A61B 5/04* (2006.01)
*A61B 5/00* (2006.01)
*A61B 5/0402* (2006.01)
*G06F 19/00* (2011.01)

(52) U.S. Cl.
CPC ............ *A61B 5/726* (2013.01); *A61B 5/0402* (2013.01); *A61B 5/04014* (2013.01); *A61B 5/7203* (2013.01); *A61B 5/7246* (2013.01); *G06F 19/322* (2013.01); *G06F 19/345* (2013.01)

(58) Field of Classification Search
CPC ... A61B 5/726; A61B 5/04014; A61B 5/0402; A61B 5/7203; A61B 5/7246; G06F 19/322; G06F 19/345
USPC ....................................................... 600/509
See application file for complete search history.

(56) References Cited

FOREIGN PATENT DOCUMENTS

CN 104102915 A 10/2014

OTHER PUBLICATIONS

Paul S. Addison. Wavelet transforms and the ECG: a review; Physiol. Meas.(2005) R155-R199. Discusses the different types of wavelet transform used in ECG analysis.*

* cited by examiner

*Primary Examiner* — Paula J Stice
(74) *Attorney, Agent, or Firm* — Steven P. Chen; Hogan Lovells US LLP

(57) ABSTRACT

The present invention provides methods and systems of using wavelet transform in a dual-track architecture to process ECG signals of patients and reference ECG signals of previously studied subjects to assess the cardiovascular health of the patients. The dual-track architecture refers to running wavelet transform on the ECG signals of the patients and the reference ECG signals to extract and analyze 2-dimensional time-domain signal characteristics of the ECG signals, and to build and analyze a 3-dimensional model of frequency-domain and time-domain information of the ECG signals. The characteristics of the ECG signals of the patients and the reference ECG signals may be compared and used to identify a cardiovascular disease of the patient or to recommend follow-up tests. The results of the comparison may also be used to configure the ECG device used to acquire the ECG signals of the patient and/or to optimize the parameters of the 2-D/3-D analysis.

26 Claims, 8 Drawing Sheets

METHODS AND SYSTEMS FOR DISEASE ANALYSIS BASED ON TRANSFORMATIONS OF DIAGNOSTIC SIGNALS

BACKGROUND OF THE INVENTION

1. Field of the Invention

The present invention relates to systems and methods for assessing the health conditions of individuals. In particular, the present invention relates to systems and methods for using wavelet transform to analyze heart diagnostic signals of individuals and to compare the analyzed results to a reference database of similarly wavelet transformed and analyzed signals to assess the cardiovascular health of the individuals and to control how the heart diagnostic signals are generated.

2. Description of Related Art

Cardiovascular disease is a serious health problem and a leading cause of death around the world. The effective treatment of cardiovascular disease depends on the early detection and diagnosis of heart abnormalities. One common tool for detecting and diagnosing cardiovascular conditions is the electrocardiogram (ECG) machine. An ECG machine uses probes that are attached to various points on a patient's limbs and chest to measure changes in electrical signals (ECG signals) generated by the patient's heartbeat. A physician may visually analyze the ECG signals to assess the health of the heart or to identify signature waveforms that may correspond to a heart disorder. One drawback of visual analyses is that subtle details in the waveforms may not be readily observable to the naked eyes, causing a mis-identification of the underlying cardiovascular condition. To improve the accuracy of diagnosis, signal processing of the ECG signals may be used to extract the finer details of the waveforms.

One such signal processing technique is using Fourier transform to transform ECG signals from the time domain to the frequency domain to extract the frequency domain information of the ECG waveforms. Such frequency domain information may include the distribution of signal energy across the frequency bands, the spectral characteristics of the frequency bands, the bandwidth of the signal energy, etc. A premise of Fourier transform analysis is that the time domain signal operated by the Fourier transform is stationary—that is, the spectral characteristics of the signal do not change with time. However, ECG signals are inherently non-stationary stochastic signals. One way to overcome the limitation of the Fourier transform is to treat an ECG signal as the superposition of many short signal segments, to run a Fourier transform on each signal segment separately, and to combine the Fourier transforms of the signal segments to construct the spectral signature of the overall signal. However, such technique is computationally intensive and thus impractical to implement.

Wavelet transform is a signal processing technique that generates information in both frequency and time domains, and is increasingly being used to process ECG signals. Wavelet transform may operate on non-stationary waveforms by using a series of scaled and translated localized oscillating base functions to orthogonally project the waveforms to a frequency domain of variable frequency resolutions. Wavelet transform may automatically adapt to the non-stationary nature of the waveforms to achieve a good balance of time-frequency resolutions. For example, a fast changing waveform may be sampled at a higher rate to achieve higher time resolution but lower frequency resolution, while a slow changing waveform may be sampled at a slower rate to achieve higher frequency resolution but lower time resolution.

While wavelet transform has been adapted to process ECG signals, it has not been fully exploited to help health professionals identify underlying physical and pathological cardiovascular conditions of the patients whose ECG signals are analyzed. In addition, results of the wavelet transform analysis have not been effectively used to configure the ECG devices to optimally capture the ECG signals of the patients. As a result, correctly diagnosing the conditions of the patients has been challenging. As such, it is desirable to have systems and methods that better use wavelet transform to analyze ECG signals to more accurately and more robustly identify cardiovascular conditions of patients. It is also desirable to use the results of the analysis to configure the ECG devices to better capture the ECG signals.

SUMMARY OF THE INVENTION

The present invention provides methods and systems of using wavelet transform to process ECG signals of patients and reference ECG signals in a dual-track architecture to identify cardiovascular conditions of the patients. The reference ECG signals are compiled from previously studied subjects and the reference ECG signal of a study subject may be associated with a diagnosed cardiovascular condition of the study subject. The reference ECG signals may be processed and compared with the ECG signals of the patients that have been similarly processed. ECG signals from the patients and from the reference database are first processed using wavelet transform to eliminate signal noise. The wavelet transformed signals may be reconstructed to generate noise-filtered ECG waveforms. The dual-track architecture refers to running a second wavelet transform on the noise-filtered ECG waveforms to extract and analyze 2-dimensional time-domain signal characteristics of the noise-filtered ECG waveforms, and to build and analyze a 3-dimensional model of frequency-domain and time-domain information of the noise-filtered ECG waveforms. The 2-D and 3-D analyzed information for the ECG signals of the patients and of the reference database are converted into coded data to facilitate comparisons between the ECG signals of the patients and the ECG signals of the reference database. The results of the comparisons may be used to assess the health of a patient such as identifying a cardiovascular disease of the patient or to recommend follow-up tests. The results of the comparison may also be used to configure the ECG device used to acquire the ECG signals of the patient to improve the acquisition of the ECG signals and/or to optimize the parameters of the 2-D/3-D analysis.

According to one embodiment of the present invention, a method executed on a processor for running a dual-track analysis of ECG signals from a patient and from a reference database to identify a medical condition is disclosed. The method includes running a first iteration of wavelet transform on a plurality of medical diagnostic signals received from the reference data source to remove noise from the plurality of medical diagnostic signals. The method also includes running a second iteration of wavelet transform on the plurality of medical diagnostic signals with the noise removed to generate a plurality of processed reference data. The method further includes running a first iteration of wavelet transform on medical diagnostic signals of a patient received from a medical diagnostic device to remove noise from the medical diagnostic signals of the patient. The method further includes running a second iteration of wavelet transform on the medical diagnostic signals of the patient with the noise removed to generate processed patient data. The method further includes analyzing the signal characteristics of the plurality of processed reference data to generate a plurality of reference signal characteristics. The method further includes analyzing the signal characteristics of the processed patient data to generate patient signal characteristics. The method further includes comparing the patient signal characteristics with the plurality of reference signal characteristics to identify a best match between the patient signal characteristics and one or more of the reference signal characteristics to help in identifying the medical condition of the patient.

According to one embodiment of the present invention, a system for a dual-track analysis of ECG signals from a patient and from a reference database to identify a medical condition is disclosed. The method includes a dual-track wavelet transform module, a signal processor module, and a comparison module. The dual-track wavelet transform module runs a first iteration of wavelet transform on a plurality of medical diagnostic signals received from a reference data source to remove noise from the plurality of medical diagnostic signals. The dual-track wavelet transform module also runs a second iteration of wavelet transform on the plurality of medical diagnostic signals with the noise removed to generate a plurality of processed reference data. The dual-track wavelet transform module further runs a first iteration of wavelet transform on medical diagnostic signals of a patient received from a medical diagnostic device to remove noise from the medical diagnostic signals of the patient. The dual-track wavelet transform module further run a second iteration of wavelet transform on the medical diagnostic signals of the patient with the noise removed to generate processed patient data. The signal processor module analyzes signal characteristics of the plurality of reference diagnostic signals to generate a plurality of reference signal characteristics. The signal processor module also analyzes signal characteristics of the processed patient data to generate patient signal characteristics. The comparison module compares the patient signal characteristics with the plurality of reference signal characteristics to identify a best match between the patient signal characteristics and one or more of the reference signal characteristics to help in identifying the medical condition of the patient.

According to one embodiment of the present invention, a non-transitory computer readable medium is disclosed. The non-transitory computer readable medium stores a plurality of reference signal characteristics that are to be compared with patient signal characteristics of a patient to help in identifying a medical condition of the patient. The plurality of reference signal characteristics is generated by a process. The process uses a first iteration of wavelet transform to transform a plurality of medical diagnostic signals received from a reference data source to remove noise from the plurality of medical diagnostic signals. The process also uses a second iteration of wavelet transform on the plurality of medical diagnostic signals with the noise removed to generate a plurality of processed reference data. The process further analyzes signal characteristics of the plurality of processed reference data to generate the plurality of reference signal characteristics.

BRIEF DESCRIPTION OF THE DRAWINGS

The accompanying drawings are provided together with the following description of the embodiments for a better comprehension of the present invention. The drawings and the embodiments are illustrative of the present invention, and are not intended to limit the scope of the present invention. It is understood that a person of ordinary skill in the art may modify the drawings to generate drawings of other embodiments that would still fall within the scope of the present invention.

DETAILED DESCRIPTION

The following paragraphs describe several embodiments of the present invention in conjunction with the accompanying drawings. It should be understood that the embodiments are used only to illustrate and describe the present invention, and are not to be interpreted as limiting the scope of the present invention.

Figure 1:
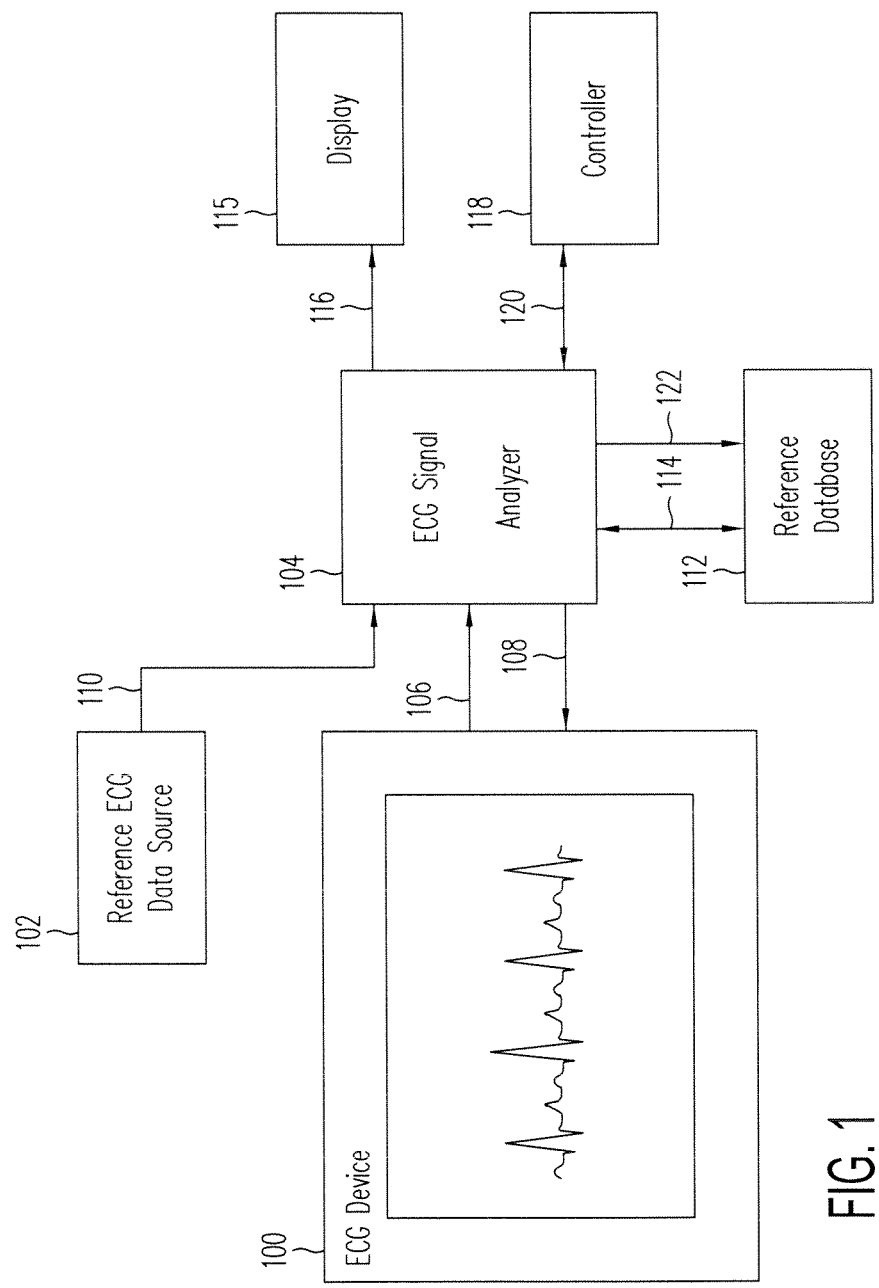
FIG. 1 shows a system block diagram of a dual-track ECG signal analyzer that is connected with an ECG device to process ECG signals of patients for comparison with a reference database of ECG signals that are similarly processed by the dual-track ECG signal analyzer for identifying cardiovascular conditions of the patients and for controlling the ECG device according to one embodiment of the present invention.

FIG. 1 shows a system block diagram of a dual-track ECG signal analyzer that is connected with an ECG device to process ECG signals of patients for comparison with a reference database of ECG signals that are similarly processed by the dual-track ECG signal analyzer for identifying cardiovascular conditions of the patients and for controlling the ECG device according to one embodiment of the present invention. An ECG device 100 may be connected to a patient through a plurality of probes that are attached to the limbs and the chest of the patient. ECG device 100 may be configured to sample the ECG signal of the patient over a programmable number of channels, for a programmable sampling duration, and using a programmable sampling mode.

ECG device 100 outputs ECG signals of patients to an ECG signal analyzer 104 through patient data connections 106. ECG signal analyzer 104 may, through ECG control bus 108, control how the ECG signals of patients are acquired by ECG device 100. For example, ECG signal analyzer 104 may process ECG signals of a patient to generate feedback control signals to adjust the number of channels, the sampling duration, the sampling mode of ECG device 100, or to reconfigure other parameters used to acquire the ECG signals of the patient. In addition to receiving ECG signals from the patient, ECG signal analyzer 104 receives a plurality of reference ECG signal waveforms from a reference ECG data source 102 over reference data input 110. Reference ECG data source 102 may be a research database that contains previously acquired ECG signals and the diagnosed cardiovascular conditions of research subjects or clinical patients who were studied or treated by hospitals or research facilities. For example, reference ECG data source 102 may include, but are not limited to, existing reference ECG databases from Massachusetts Institute of Technology-Beth Israel Hospital (MIT-BIH), American Heart Association (AHA), Physikalisch-Technische Bundesanstalt (PTB), etc., containing ECG signals of patients with known arrhythmias and/or cardiovascular conditions. In one or more embodiments, reference ECG data source 102 may contain the ECG signals of previously studied patients collected from ECG device 100 and their cardiovascular conditions. In other embodiments, reference ECG data source 102 may contain a combination of data from existing reference ECG databases and from newly studied patients. ECG signal analyzer 104 may process the ECG data from reference ECG data source 102 to perform 2-D analyses to identify time-domain signal characteristics, and to perform 3-D analyses to identify time-domain and frequency-domain signal information of the reference ECG signal waveforms. In one or more embodiments, ECG signal analyzer 104 may perform wavelet transform on the ECG data to generate processed data for the 2-D and 3-D analyses. Using pattern recognition, stereo matching, or other feature recognition techniques, ECG signal analyzer 104 or a controller 118 may process the time-domain signal characteristics, and the time-domain and frequency-domain signal information of the reference ECG signals of study subjects who have been diagnosed with a cardiovascular condition to classify or identify signal characteristics that may be associated with the diagnosed cardiovascular condition. ECG signal analyzer 104 may store the ECG signal characteristics associated with a variety of diagnosed cardiovascular conditions in a reference database 112 through a reference data bus 114.

ECG signal analyzer 104 similarly processes the patients' ECG signals from ECG device 100 to perform 2-D analyses to extract time-domain characteristics, and to perform 3-D analyses to extract time-domain and frequency-domain information of the patients' ECG waveforms. The extracted time-domain characteristics, and the extracted time-domain and frequency-domain information of a patient's ECG waveforms may be compared with the signal characteristics associated with the myriad of diagnosed cardiovascular conditions stored in reference database 112 to identify the mostly likely cardiovascular condition of the patient. For example, the patient may be identified as having, with a certain probability, the cardiovascular condition associated with the signal characteristics from reference database 112 exhibiting the closest match with the extracted information from the patient's ECG waveform. In one or more embodiments, the signal characteristics of the patient's ECG waveforms may be compared with a myriad of reference signal characteristics in reference database 112 even if the reference signal characteristics are not associated with any cardiovascular conditions. To facilitate the comparison, the signal characteristics associated with each cardiovascular condition, or even signal characteristics that are not associated with any cardiovascular conditions, from reference database 112 may be converted, or encoded into coded reference data containing a number of data fields; similarly, extracted information from patients may be converted, or encoded into coded patient data containing the same data fields. The values of the data fields from the coded reference data and the coded patient data may be compared. ECG signal analyzer 104 may access reference database 112 to read or write coded reference data using address bus 122.

ECG signal analyzer 104 may output ECG waveforms, time-domain signal characteristics, time-domain and frequency-domain information extracted from the ECG waveforms, 3-D models from the 3-D analyses, coded reference data, coded patient data, information on the identified cardiovascular conditions, and/or other information of the patient to a display 115 through an output bus 116. Controller 118 may control the operation of ECG signal analyzer 104, perform some of the 2-D and 3-D analyses, classify signal characteristics of reference ECG signals associated with cardiovascular conditions, encode the results from the 2-D and 3-D analyses into coded reference and patient code, compare the coded reference and patient code, and perform other operations. Controller 118 may communicate with ECG signal analyzer 104, and may also control the operation of ECG signal analyzer 104 through a controller bus 120. In one or more embodiments, ECG signal analyzer 104 may be implemented as an application specific integrated circuit (ASIC), a programmable logic array, a processor executing software or firmware stored on a storage medium, or a combination thereof. Controller 118 may be a microprocessor or a microcontroller executing software or firmware stored in memories, a programmable logic array, or implemented as a combination of hardware, software, and firmware.

Figure 2:
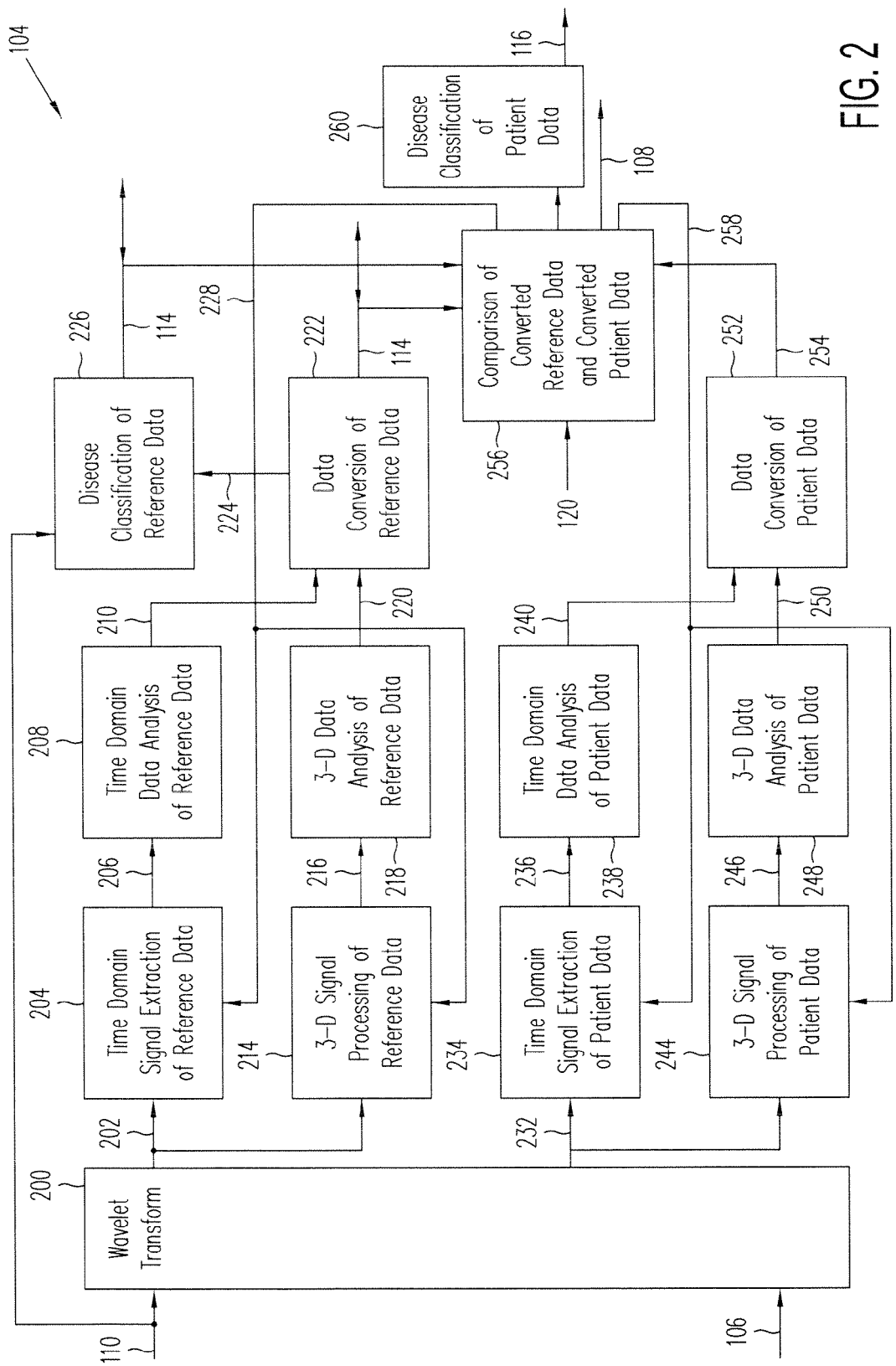
FIG. 2 shows a system block diagram of the dual-track ECG signal analyzer of FIG. 1 using wavelet transform to perform 2-D time-domain analyses and 3-D time-domain and frequency-domain analyses of the ECG signals of the patient and the reference ECG signals to identify cardiovascular conditions of the patient according to one embodiment of the present invention.

FIG. 2 shows a system block diagram of the dual-track ECG signal analyzer 104 of FIG. 1 using wavelet transform to perform 2-D time-domain analyses and 3-D time-domain and frequency-domain analyses of the ECG signals of the patient and the reference ECG signals to identify cardiovascular conditions of the patient according to one embodiment of the present invention. In one interpretation, the term "dual-track" may refer to the analyses of the ECG signals in both 2-D time-domain and 3-D time-domain and frequency-domain. In another interpretation, "dual-track" may refer to the processing of both the ECG signals of the patient and the reference ECG signals. A wavelet transform module 200 performs wavelet transform on either reference ECG signals from reference ECG data source 102 received over reference data input 110 or the ECG signals of patients from ECG device 100 received over patient data connection 106. The ECG signals may be corrupted by noise such as electrical contact noise, artifact introduced by breathing or motion of the patients or subjects whose ECG signals are taken, etc. The ECG signals may also be corrupted by interference sources in the test environment operating in the same bandwidth as the ECG signals, such as other ECG devices or other types of medical devices. Wavelet transform module 200 decomposes the ECG signals to an orthogonal space of time and frequency projections. Time and frequency projections containing noise may be removed or attenuated and the resulting noise-filtered decomposed signals may be inversely transformed back into the time domain to reconstruct the ECG signals. The reconstructed ECG signals have a higher signal-to-noise ratio and may be output from wavelet transform module 200 to undergo another iteration of wavelet transform to decompose the reconstructed ECG signals. Thus, the ECG signals of the patient and the reference ECG signals may undergo two iterations of wavelet transform to improve the extraction of their signal characteristics. The reconstructed reference ECG signals may be output on bus 202 for a second iteration of wavelet transform, and subsequent time domain signal extraction and analysis, and 3-D signal processing and analysis of the reference data. The reconstructed patient ECG signals may similarly be output on bus 232 for a second iteration of wavelet transform, and subsequent time domain signal extraction and analysis, and 3-D signal processing and analysis of the patient data.

Figure 3:
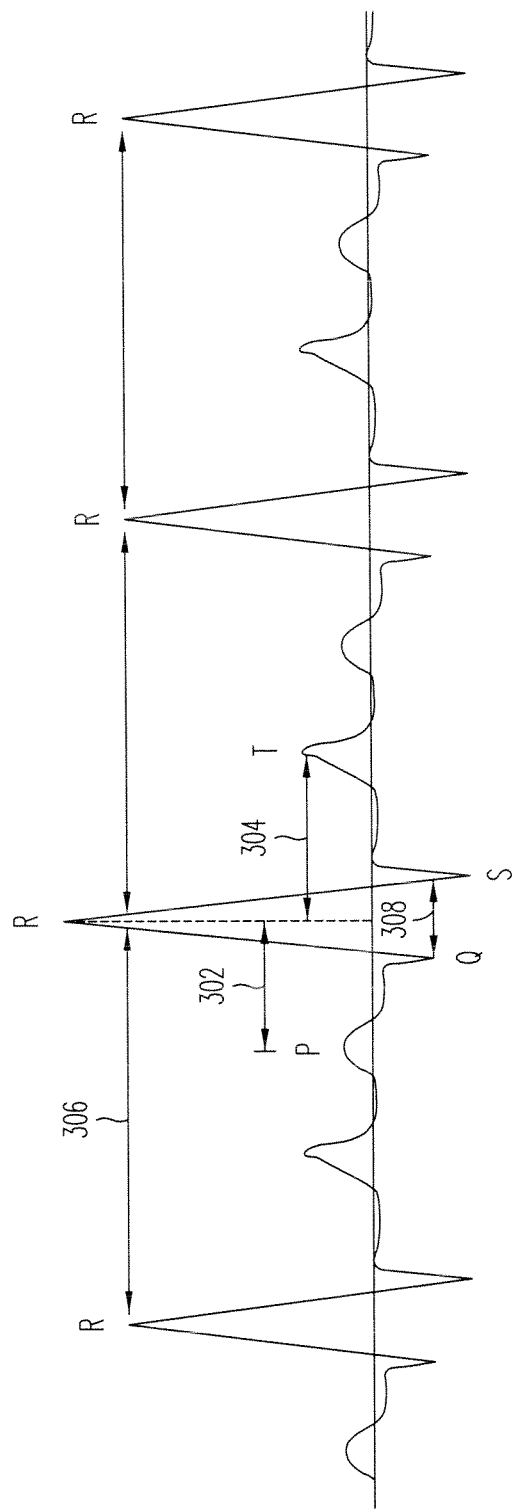
FIG. 3 shows an example of the P, Q, R, S, T features of a noise-filtered reconstructed ECG signal waveform from the patient or from the reference database according to one embodiment of the present invention.

A time domain signal extraction of reference data module 204 performs wavelet transform on the reconstructed reference ECG signals received on bus 202 to decompose the signals into time and frequency projections of varying time resolution, and processes the wavelet transform decomposition of the reconstructed reference ECG signals to identify time domain signal characteristics of the reference data. For example, ECG signals contain periodic waveforms where each cycle of the waveforms may be marked by features identified as P, Q, R, S, T. FIG. 3 shows an example of the P, Q, R, S, T features of a noise-filtered reconstructed ECG signal waveform from the patient or from the reference database according to one embodiment of the present invention. The position, shape, amplitude of the P, Q, R, S, T features and the timing relationship between them may be used as markers of various cardiovascular conditions. For example, the average time delays between the P and the R features labeled 302, the average delays between the R feature and the T feature labeled 304, the average delays between two successive R features labeled 306, the width of the QRS complex labeled 308, or the amplitude of the R feature may all be distinctive of the cardiovascular health of a patient.

FIG. 3 may also represent a slice of the decomposition of the reconstructed reference ECG signals along the time axis for a given frequency band of the time and frequency projections after wavelet transform. The time resolution of the decomposed waveform is inversely related to the frequency resolution of the frequency slice. For example, at high frequencies, the time resolution is finer and the frequency resolution is coarser. On the other hand, at lower frequencies, the time resolution is coarser and the frequency resolution is finer. To better resolve the delays between the P, Q, R, S, T features, it may be desirable to use a frequency slice of the time and frequency projects at the higher frequency range to obtain finer time resolution. Conversely, to better resolve the shape and amplitude of the P, Q, R, S, T features, it may be desirable to use a frequency slice of the time and frequency projections at the lower frequency range to obtain finer frequency resolution.

Referring back to FIG. 2, module 204 may analyze the P, Q, R, S, T features of the time-domain projections of the wavelet transform decomposition of the reconstructed reference ECG signals using various feature extraction methods. For example, the complex comprising the Q, R, S features is the most prominent complex of the ECG signals, exhibiting a large amplitude and a distribution of energies in the mid to high frequency bands. Module 204 may identify the QRS complex in the time domain by comparing the peak of the QRS complex with a detection threshold. Once the QRS complex is identified, module 204 may use the R peak of the QRS complex as a reference point to identify the P and T features or other features of the ECG signals. In one or more embodiments, module 204 may analyze the first order and the second order time derivatives of the wavelet transform decomposition of the reconstructed reference ECG signals to identify distinctive time slope and the rate of change in the time slope associated with the QRS complex to locate the vertices of the QRS complex.

In other embodiments, module 204 may analyze the wavelet transform decomposition of the reconstructed reference ECG signals in the frequency domain to extract the time domain signal characteristics of the reference data. For example, module 204 may identify the QRS complex in the frequency domain by detecting the energy distribution of the frequency bands of the QRS complex, or the difference in the energy distribution between the QRS complex and that of the P and T features. In one or more embodiments, module 204 may integrate the energies in the mid to high frequency bands to improve the signal-to-noise ratio. Module 204 may have a discriminator circuit to detect the energies of the QRS complex as distinguished from the energies of the P and T features by comparing the energies with a detection threshold. In one or more embodiments, module 204 may extract other characteristics of the QRS complex in both the frequency domain and the time domain such as by calculating the surface area of the energy distribution to identify the QRS complex. As before, once the QRS complex is identified, module 204 may identify other features of the ECG signals. Module 204 may output the time domain signal characteristics of the reference data on a data bus 206.

A time domain data analysis of reference data module 208 analyzes the extracted time domain signal characteristics of the reference data received on bus 206 to identify characteristics that may be used to classify cardiovascular conditions. For example, module 208 may analyze parameters such as the distribution or the mean of the time difference between successive R peaks, the distribution or the mean of the amplitudes of the R peaks, the distribution or the mean of the width of the QRS complexes, the relationship between these parameters, etc. Different cardiovascular conditions such as coronary artery disease, ischemia, myocardial infarction, etc., may exhibit distinctive characteristics in these parameters. These parameters may be used by autonomous classification techniques such as statistical pattern recognition, artificial neural network, syntactic structure pattern recognition, fuzzy pattern recognition, etc., to generate classification rules to classify the reference data. The classification rules may then be applied to the patient ECG signals to generate a likelihood or probability that the patient has a cardiovascular condition. Module 208 may output the results of the time domain analysis on a data bus 210.

In parallel with the time domain signal extraction and analysis of the reconstructed reference ECG signals, a 3-D signal processing of reference data module 214 performs wavelet transform on the reconstructed reference ECG signals received on bus 202 to decompose the signals into time and frequency projections, and processes the wavelet transform decomposition of the reconstructed reference ECG signals to identify time-domain and frequency-domain signal information of the reference data. The decomposition of the reconstructed reference ECG signals comprises the 3-D orthogonal time and frequency projections of the reconstructed reference ECG signals.

Figure 4:
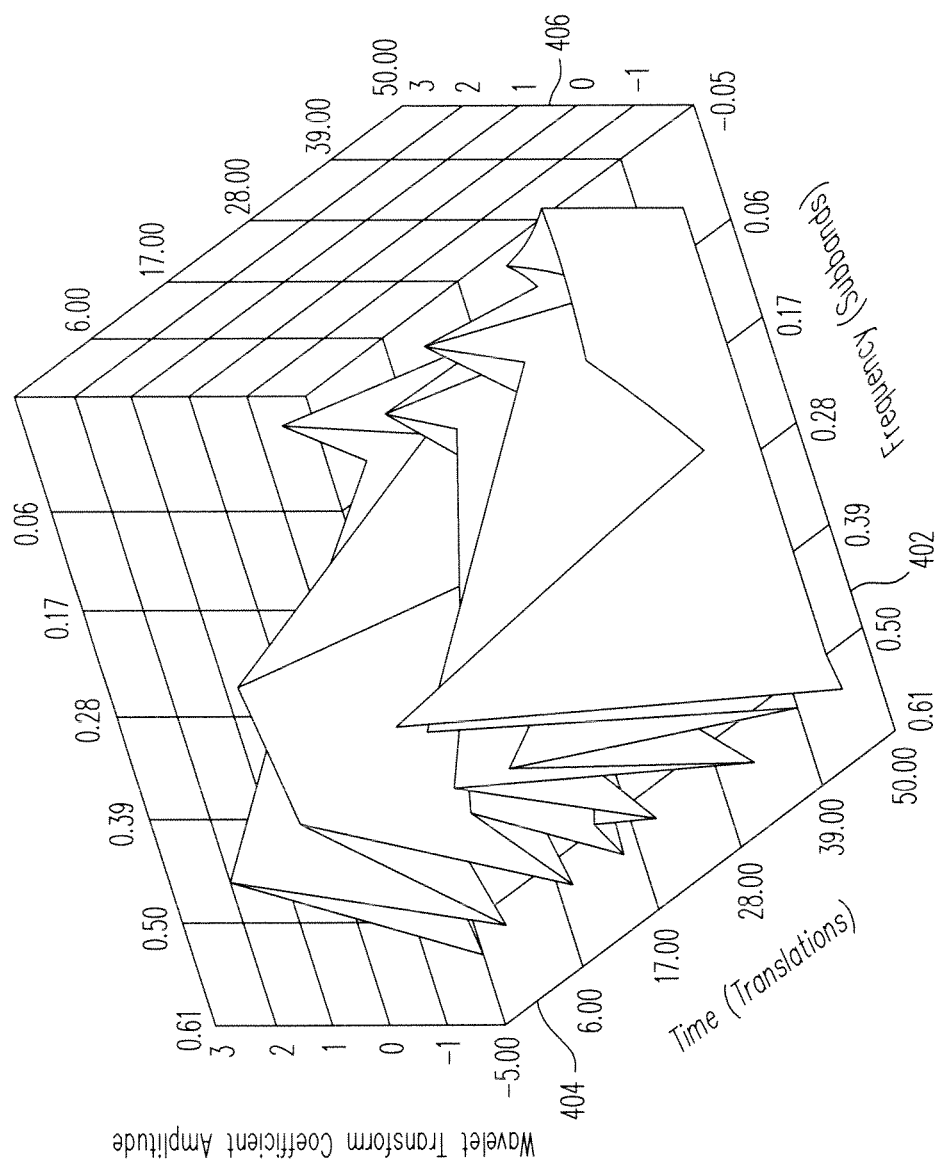
FIG. 4 shows the 3-D orthogonal time and frequency projections of the wavelet transform decomposition of the reconstructed reference ECG signals or of the reconstructed patient ECG signals according to one embodiment of the present invention.

FIG. 4 shows the 3-D orthogonal time and frequency projections of the wavelet transform decomposition of the reconstructed reference ECG signals or of the reconstructed patient ECG signals according to one embodiment of the present invention. Along a first dimension 402 are the frequency bands containing the energy spectrum of the ECG data. The frequency bands may have different frequency resolution and thus different corresponding time resolution. For example, frequency bands in the higher frequency range may have coarser frequency resolution and correspondingly finer time resolution. Conversely, frequency bands in the lower frequency range may have finer frequency resolution and correspondingly coarser time resolution. Along a second dimension 404 are the time translations or displacement of features of the ECG data. The frequency bands along the different slices of time translations represent the frequency content of features of the ECG signals at varying frequency resolution across the frequency range for each time translation and have amplitudes or coefficients along a third dimension 406. Similarly, the time translations along the different slices of frequency bands represent the time displacement of features of the ECG signals at varying time resolution across the frequency bands and also have coefficients along third dimension 406. Therefore, the 3-D orthogonal time and frequency projections represent the distribution of energy of the features of the ECG signals across the range of frequency bands and time translations. The range of the frequency bands, the resolution for each of the frequency bands, the range of the time translation, and the resolution of the time translation may be configured to improve the identification of the time-domain and frequency-domain signal information of the ECG data.

Referring back to FIG. 2, module 214 may process the reference data in two levels. In a first level, module 214 may characterize the reference data in the frequency domain. For example, module 214 may analyze the energy spectrum of the reference data such as the ordering of time displacement of the features corresponding to the frequency band of a frequency slice where the frequency band contains significant energies, the highest coefficients and their corresponding time displacement for each frequency band across the bands of the frequency domain, etc. In a second level, module 214 may characterize the frequency bands in the time domain. For example, module 214 may calculate the surface area for each frequency band across all the frequency bands corresponding to each time translation, identify the peak surface area and/or the trough surface area of the frequency bands for each time translation, identify the highest coefficient and/or the lowest coefficient of the frequency bands for each time translation, etc. In one or more embodiments, module 214 may identify the peak surface area and/or the trough surface area of the frequency bands and their corresponding time displacements across the 3-D time and frequency space. Module 214 may output the extracted time-domain and frequency-domain signal information of the reference data on bus 216.

Similar to the time domain analysis by module 208, a 3-D data analysis of reference data module 218 analyzes the extracted time-domain and frequency-domain signal information of the reference data received on bus 216 to identify signal characteristics for classifying cardiovascular conditions. For example, module 218 may perform zero-crossing analysis, corner detection, 3-D graphic stereo matching of the surface areas or the coefficients of the frequency bands across the time translations, etc. Multi-dimensional analysis of signal characteristics in both the frequency and time domains of the non-stationary ECG reference data captures signal characteristics that may be difficult to discern in the frequency domain or the time domain alone. Module 218 may output the results of the time-domain and frequency-domain analysis on a data bus 220.

To reduce the amount of data needed to represent the signal characteristics of the reference data, and to facilitate the classification and comparison of the signal characteristics between the reference data and the patient data, the signal characteristics may be compressed, encoded, or converted into coded data. A data conversion of reference data module 222 converts the signal characteristics of the reference data from the time domain analysis and from the 3-D analysis into coded reference data. For example, the coded reference data may include the N largest amplitudes of the signal characteristics from the 3-D analysis and their corresponding frequency bands and time displacements. The coded reference data may also encode parameters used to extract and analyze the reference data, such as the detection threshold for the QRS complex, information about the source of the reference data, a unique identifier used to identify the reference data, etc. The coded reference data may contain different encoded fields for the signal characteristics from the time domain analysis and the 3-D analysis because the two analyses may have different resolution. Depending on the desired level of granularity of the comparison between the reference data and the patient data, it may be faster to compare only one of the time-domain and 3-D encoded fields if the resolution of the comparison from comparing only one encoded field is acceptable. In one or more embodiments, the signals characteristics from the two analyses may be encoded into the same field to minimize the size of reference database 112. In one or more embodiments, to further reduce storage space and/or to accelerate the comparison, module 222 may store into reference database 112 coded reference data encoded from signal characteristics that are representative of a classified cardiovascular condition instead of storing all coded reference data. Module 222 may output the coded reference data on data bus 114 for writing into reference database 112 and may also present the coded reference data on data bus 224 for disease classification. In one or more embodiments, the signal characteristics of the reference data may not be converted into coded data. Module 222 may output the un-encoded signal characteristics of the reference data on data bus 114 for writing into reference database 112 and may present the un-encoded signal characteristics on data bus 224 for disease classification.

A disease classification of reference data module 226 receives a plurality of coded and/or un-encoded reference data and their associated diagnosed cardiovascular condition to classify or determine characteristics of the coded or un-encoded reference data that may be used to identify the various diagnosed cardiovascular conditions. Module 226 may use autonomous classification techniques such as statistical pattern recognition, artificial neural network, syntactic structure pattern recognition, fuzzy pattern recognition, etc., to synthesize classification rules that may be applied to coded or un-encoded patient data to identify the patient as suffering from a corresponding cardiovascular condition. For example, module 226 may generate a range of values for the fields encoding the signal characteristics from the time domain analysis and the 3-D analysis as corresponding to a certain probability of a cardiovascular condition. When a patient with unknown conditions has a coded field value that falls within the range for the field, the patient may be diagnosed as having the corresponding cardiovascular condition with the specified probability. In one or more embodiments, module 226 may pair a coded or un-encoded reference data and its associated diagnosed cardiovascular condition received from reference ECG data source 102 and may write the paired data on data bus 114 for writing into reference database 112. In one or more embodiments, module 226 may output the range of values for the encoded or un-encoded fields classified as corresponding to a cardiovascular condition, along with the probability that the value range corresponds to the cardiovascular condition, on data bus 114 for writing into reference database 112.

In one or more embodiments, coded or un-encoded reference data may not be associated with any diagnosed cardiovascular conditions. If these coded or un-encoded reference data have field values that do not fall within the ranges for any classified cardiovascular conditions, module 226 may still generate classification rules for these coded or un-encoded reference data to identify any common characteristics among them. If common characteristics are found, researchers and health care professionals may perform further studies on study subjects exhibiting these common characteristics to identify any associated abnormalities.

As shown in FIG. 2, ECG signal analyzer 104 includes analogous modules to extract, analyze, and convert patient data. These modules may operate similarly as the modules for the reference data. For example, a module 234 performs wavelet transform on the reconstructed patient ECG signals received on bus 232 to decompose the signals into time and frequency projections of varying time resolution, and processes the wavelet transform decomposition of the reconstructed patient ECG signals to identify time domain signal characteristics of the patient data that are output on a bus 236; a module 238 analyzes the extracted time domain signal characteristics of the patient data received on bus 236 and outputs the analyzed time domain signal characteristics of the patient data on a data bus 240; a module 244 performs wavelet transform on the reconstructed patient ECG signals received on bus 232 to decompose the signals into time and frequency projections, and processes the wavelet transform decomposition of the reconstructed patient ECG signals in 3-D to identify time-domain and frequency-domain signal information of the patient data that are output on a data bus 246; a module 248 analyzes the 3-D extracted time-domain and frequency-domain signal information of the patient data received on bus 246 and outputs the results of the time-domain and frequency-domain analysis on a data bus 250; and a module 252 converts the signal characteristics of the patient data from the time domain analysis received on bus 240 and the signal characteristics of the patient data from the 3-D analysis received on bus 250 into coded patient data. In one or more embodiments, module 252 may not convert the signal characteristics of the patient data. The coded or un-encoded patient data may be output on bus 254. A detail description of these modules will not be repeated for the sake of brevity. In one or more embodiments, a single set of modules may be time shared or multiplexed to extract, analyze, and convert both the reference data and the patient data.

A module 256 compares the coded or un-encoded reference data with the coded or un-encoded patient data to determine if there is a sufficient match to indicate that the patient may have a cardiovascular condition associated with the matching coded reference data. Module 256 may receive the coded or un-encoded patient data over data bus 254 and may read the coded or un-encoded reference data and the associated cardiovascular condition from reference database 112 over bus 114. In one or more embodiments, module 256 may compare the values of the encoded fields encoding the signal characteristics from the time domain analysis and the 3-D analysis of the coded patient data with the corresponding encoded fields from a series of coded reference data retrieved from reference database 112. Techniques for the comparison may include correlation, statistical pattern matching, Euclidean distance calculation, and other types of similarity assessment to generate a measure of the match between the values for each encoded field. The results of the comparisons for the two encoded fields encoding the time domain and 3-D signal characteristics may be summed to generate an overall score. Module 256 may sort the scores from the comparisons of the coded patient data with the multiple coded reference data to find the highest score and to declare the coded reference data giving rise to the highest score as the best match.

In one or more embodiments, module 256 may perform a two-step process by initially comparing the multiple scores with a programmable detection threshold to screen for scores that exceed the threshold followed by sorting to find the highest score. If no score exceeds the threshold, no match is declared. Module 256 may generate a feedback signal on ECG control bus 108 to adjust the parameters of ECG device 100 such as the number of channels, the sampling duration, the sampling mode, etc., to resample the patient ECG signal waveforms and to make another attempt at finding a best match. In one or more embodiments, controller 118 of FIG. 1 may also configure the parameters of ECG device 100. Module 256 may receive the configuration data from controller 118 over controller bus 120 and may multiplex the received configuration data on ECG control bus 108.

In one or more embodiments, module 256 may adjust the parameters used during the signal extraction of the reference data and the patient data in the time domain by module 204 and 234 such as the detection threshold used for identifying the QRS complex. In one or more embodiments, module 256 may adjust the detection threshold that is compared with the energies in certain frequency bands occupied by the QRS complex in the frequency domain to identify the QRS complex. In one or more embodiments, module 256 may adjust the parameters used by the 3-D signal processing of module 214 and 244 to extract time-domain and frequency-domain signal information of the reference data and the patient data such as the frequency range, frequency resolution or time resolution, range of time translation, etc. Module 256 may adjust the parameters for extracting the reference ECG data through bus 228. Similarly, module 256 may adjust the parameters for extracting the patient ECG data through bus 258 so that the signal characteristics of the patient ECG data may be re-extracted without resampling the patient ECG signal waveforms.

Because the signal characteristics from the time domain analysis and the 3-D analysis may have different granularity of information, their encoded fields also may have different granularity of information. In one or more embodiments, if a comparison of the signal characteristics from the time domain analysis such as time displacements and amplitudes of the features of the ECG signals is desired in exchange for speed, module 256 may compare only the encoded field encoding the signal characteristics from the time domain analysis. In one or more embodiments, module 256 may compare the encoded field encoding the signal characteristics in the time and frequency domains from the 3-D analysis. For example, module 256 may compare the encoded field encoding the N largest amplitudes of the signal characteristics from the 3-D analysis and their corresponding frequency bands and time displacements. In one or more embodiments, to achieve a finer granularity of comparison, module 256 may compare the encoded amplitudes or surface areas of frequency bands at each slice of time displacement, or compare the encoded amplitudes or shapes of time displacements at each slice of frequency band. In one or more embodiments, the encoded field for the coded reference data has a range of values corresponding to a certain probability of a cardiovascular condition. If the value in the encoded field of the coded patient data falls within the range, the patient may be diagnosed as having the corresponding cardiovascular condition with the specified probability.

Figure 5:
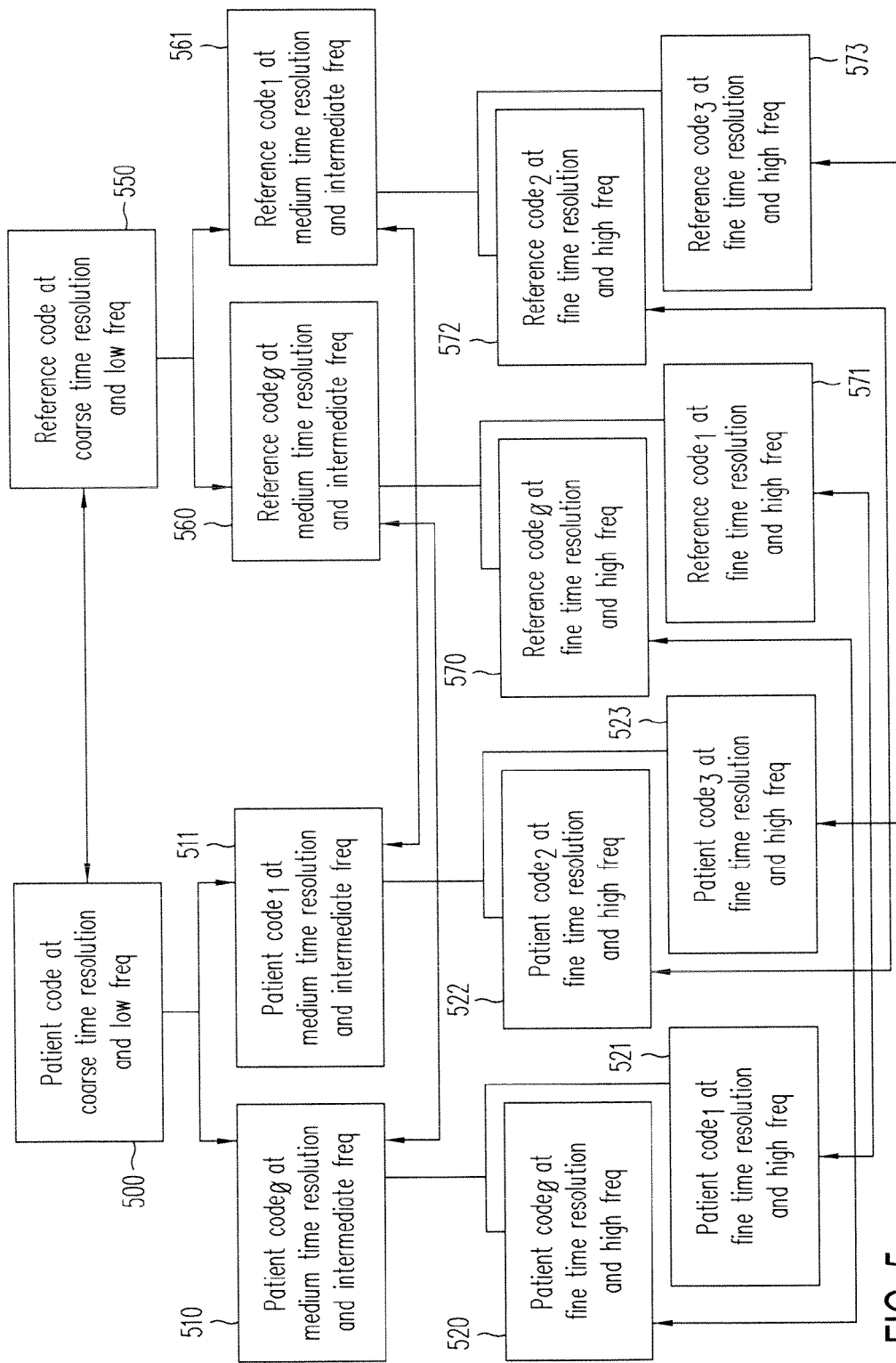
FIG. 5 shows a matrix comparison of the un-encoded patient data and the un-encoded reference data from the 3-D analyses at different levels of details as determined by the granularity of the desired time resolution and corresponding frequency resolution according to one or more embodiments of the present invention.

In one or more embodiments, module 256 may compare the un-encoded signal characteristics of the reference data from the 3-D analysis with the un-encoded signal characteristics of the patient data from the 3-D analysis using a matrix comparison technique. FIG. 5 shows a matrix comparison of the un-encoded patient data and the un-encoded reference data from the 3-D analyses at different levels of details as determined by the granularity of the desired time resolution and corresponding frequency resolution according to one or more embodiments of the present invention. The matrix comparison may be divided into a hierarchy of levels of comparison with each level comparing data at a different level of details. As discussed with respect to FIG. 4, the 3-D time and frequency projections of the wavelet transform of the ECG signals range from lower frequency bands of fine frequency resolution and coarse time resolution to higher frequency bands of coarse frequency resolution and fine time resolution. The matrix comparison may compare different slices of frequency bands and their corresponding frequency resolution and time resolution at different levels in the hierarchy. For example, referring to FIG. 5, the top level of the matrix comparison compares the patient data 500 and reference data 550 at the low frequency range and correspondingly coarse time resolution. At this coarse time resolution, some features of the 3-D projections of the patient data 500 and reference data 550 at different time displacements may be discerned and compared. If finer time resolution is desired, the matrix comparison may go down to the second level to compare the coded patient data 510, 511 and coded reference data 560, 561 at the intermediate frequency range and correspondingly medium time resolution. If even finer time resolution is desired, the matrix comparison may go down to the third level to compare the coded patient data 520, 521, 522, 523 and coded reference data 570, 571, 572, 573 at the high frequency range and correspondingly fine time resolution.

In one or more embodiments, the top level of the matrix comparison may compare the patient data and reference data at the high frequency range and correspondingly coarse frequency resolution. At this coarse frequency resolution, some features of the 3-D projections of the patient data and reference data at the intermediate frequency range may be identified. If finer frequency resolution is desired, the matrix comparison may go down one level to compare the patient data and reference data at the intermediate frequency range and correspondingly medium frequency resolution. At this medium frequency resolution, some features of the projections of the patient data and reference data at the low frequency range may be identified. If even finer frequency resolution is desired, the matrix comparison may go down yet one more level to compare the patient data and reference data at the low frequency range and fine frequency resolution. Thus, the comparison of the coded reference data and the coded patient data may be achieved at the desired level of detail.

A disease classification of patient data module 260 analyzes the result of the comparisons of the coded reference data and coded patient data and/or the result of the comparison of the un-encoded reference data and un-encoded patient data to identify a cardiovascular condition of the patient. For example, module 260 may declare the patient as having the cardiovascular condition associated with the coded or un-encoded reference data giving rise to the highest matching score. In one or more embodiments, there may be a probability associated with the identified cardiovascular condition. In one or more embodiments, when the coded or un-encoded reference data for a cardiovascular condition has a range of values corresponding to a certain probability of that cardiovascular condition, the ranges of values for the coded or un-encoded reference data associated with different cardiovascular conditions with various corresponding probabilities may overlap. If the value in the coded or un-encoded patient data falls within the overlapping ranges, the patient may be diagnosed as having any one of the several cardiovascular conditions with the specified probabilities. Follow-up tests may be recommended to identify which of the detected cardiovascular conditions is the most likely. In one or more embodiments, once a cardiovascular condition is identified, an image of the heart corresponding to the cardiovascular condition may be generated. Module 260 may output the ECG signal waveform of the patient, the reference ECG signal waveform corresponding to the encoded or un-encoded reference data with the best match, one or more diagnosed cardiovascular conditions, the probabilities associated with the one or more cardiovascular conditions, images of the heart corresponding to the one or more cardiovascular conditions, etc., to display 115 through output 116.

Figure 6:
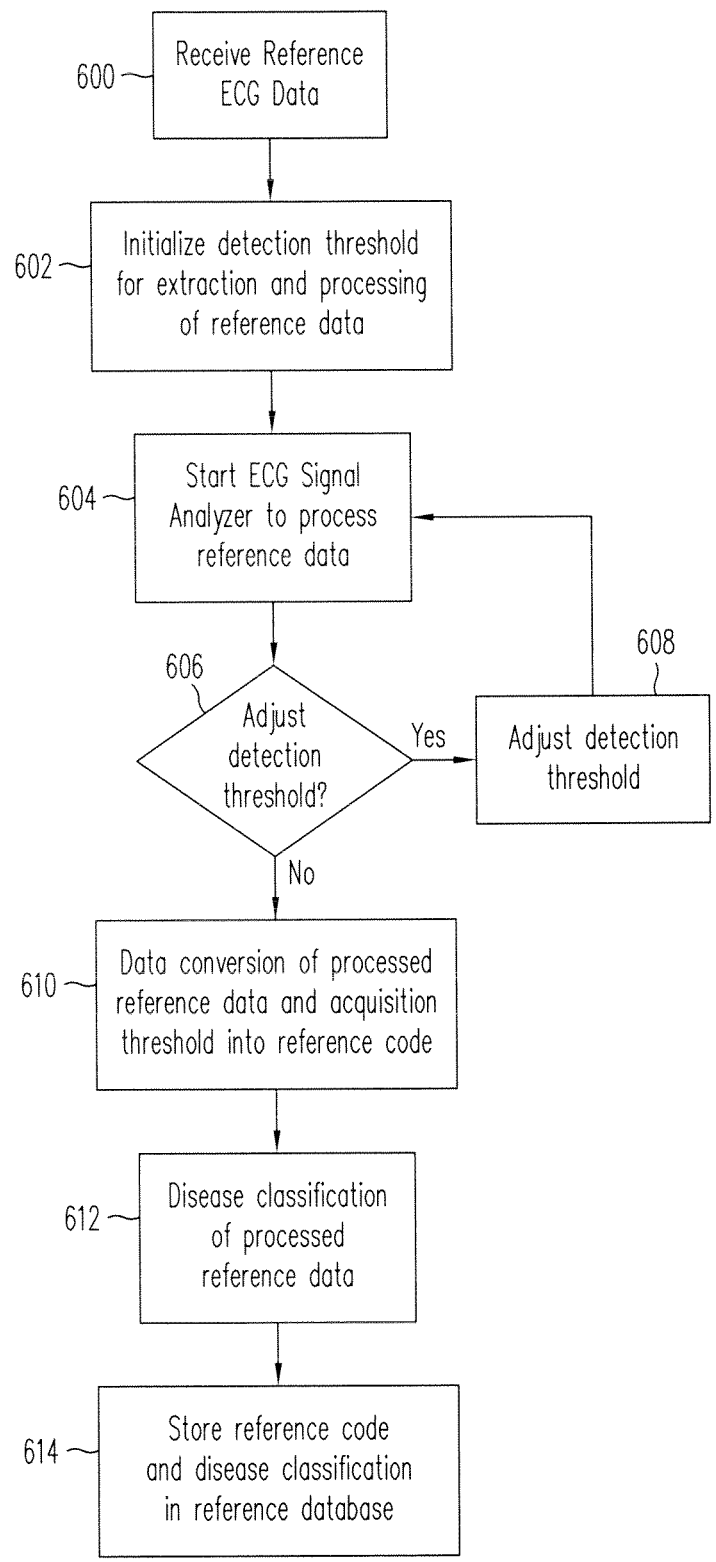
FIG. 6 shows a flow chart of the processing of the ECG reference signals by the dual-track ECG signal analyzer to create the reference database and to control the acquisition process of the ECG reference signals according to one embodiment of the present invention.

FIG. 6 shows a flow chart of the processing of the ECG reference signals by dual-track ECG signal analyzer 104 to create the reference database and to control the acquisition process of the ECG reference signals according to one embodiment of the present invention. In 600, the method receives reference ECG signals from a reference ECG data source. In one or more embodiments, step 600 may receive the diagnosed cardiovascular conditions associated with the reference ECG signals. The dual-track ECG signal analyzer may use pattern recognition to classify or identify signal characteristics of the reference ECG signals associated with the cardiovascular conditions. The classified signal characteristics may be used as signatures to detect cardiovascular conditions of patients whose ECG signal waveforms exhibit similar signal characteristics.

In 602, the process initializes the detection threshold used for extracting and processing the reference ECG signals. For example, 602 may initialize the detection threshold to be compared with the peak of the QRS complex in the time domain to identify the QRS complex in the reference ECG signals. In one or more embodiments, 602 may initialize the detection threshold to be compared with the energies in certain frequency bands occupied by the QRS complex in the frequency domain to identify the QRS complex. In one or more embodiments, 602 may initialize other parameters that are used to extract and process the reference ECG signals such as the frequency range, frequency resolution or time resolution, range of time translation, etc., used by the 3-D signal processing of the reference ECG signals.

In 604, the process starts ECG signal analyzer 104 to process the reference ECG signals. ECG signal analyzer 104 may use wavelet transform to perform 2-D analyses to identify time-domain signal characteristics, and 3-D analyses to identify time-domain and frequency-domain signal information of the reference ECG signal waveforms. ECG signal analyzer 104 may perform a first iteration of the wavelet transform to remove or attenuate noise from the reference ECG signals, reconstruct the noise-filtered reference ECG signals in the time domain, perform a second iteration of the wavelet transform on the reconstructed noise-filtered reference ECG signals, process/extract/analyze the wavelet transform decomposition of the reconstructed reference ECG signals using the detection threshold to identify time domain signal characteristics of the reference ECG signals, and perform 3-D analyses to extract 3-D time-domain and frequency-domain information of the reference ECG signals.

In 606, the process determines if the detection threshold needs to be adjusted. For example, if the detection threshold is set too high such that no QRS complex is detected in the reconstructed reference ECG signals, the detection threshold may have to be adjusted downward. On the other hand, if the detection threshold is set too low such that false QRS complexes are detected (e.g., the delay between successive R peaks is too short), the detection threshold may have to be adjusted upward. In 608, the process adjusts the detection threshold. In 604, the process uses the new detection threshold to re-extract and reprocess the reference ECG signals.

In 610, the process converts the signal characteristics of the reference ECG signals from the time domain analyses and from the 3-D analyses into coded reference data to facilitate the classification of the signal characteristics and the comparison of the signal characteristics of the reference ECG signals with those of the patient ECG signals. In one or more embodiments, the classification and comparison may be performed using un-encoded signal characteristics of the reference ECG signals. The process may also encode the detection threshold for the QRS complex, and other parameters used in the signal extraction and processing steps.

In 612, the coded or un-encoded reference data associated with a diagnosed cardiovascular condition are processed to classify or identify characteristics of the coded or un-encoded reference data that may correspond with the diagnosed cardiovascular conditions. In one or more embodiments, 612 may process the time domain and 3-D signal characteristics of the reference ECG signals associated with a diagnosed cardiovascular condition to identify features of the signal characteristics that may correspond with the diagnosed cardiovascular conditions. The identified characteristics or features may include a probability that a patient whose ECG signals exhibit the identified characteristics or features is likely to have the corresponding cardiovascular condition.

In 614, the process stores the coded or un-encoded reference data, the associated cardiovascular conditions, the characteristics of the coded or un-encoded reference data corresponding to the cardiovascular conditions, and the associated probability in reference database 112. The coded or un-encoded reference data or the characteristics of the coded or un-encoded reference data corresponding to the cardiovascular conditions may be compared with the coded or un-encoded patient data derived from a patient's ECG signals to detect the cardiovascular condition of the patient.

Figure 7:
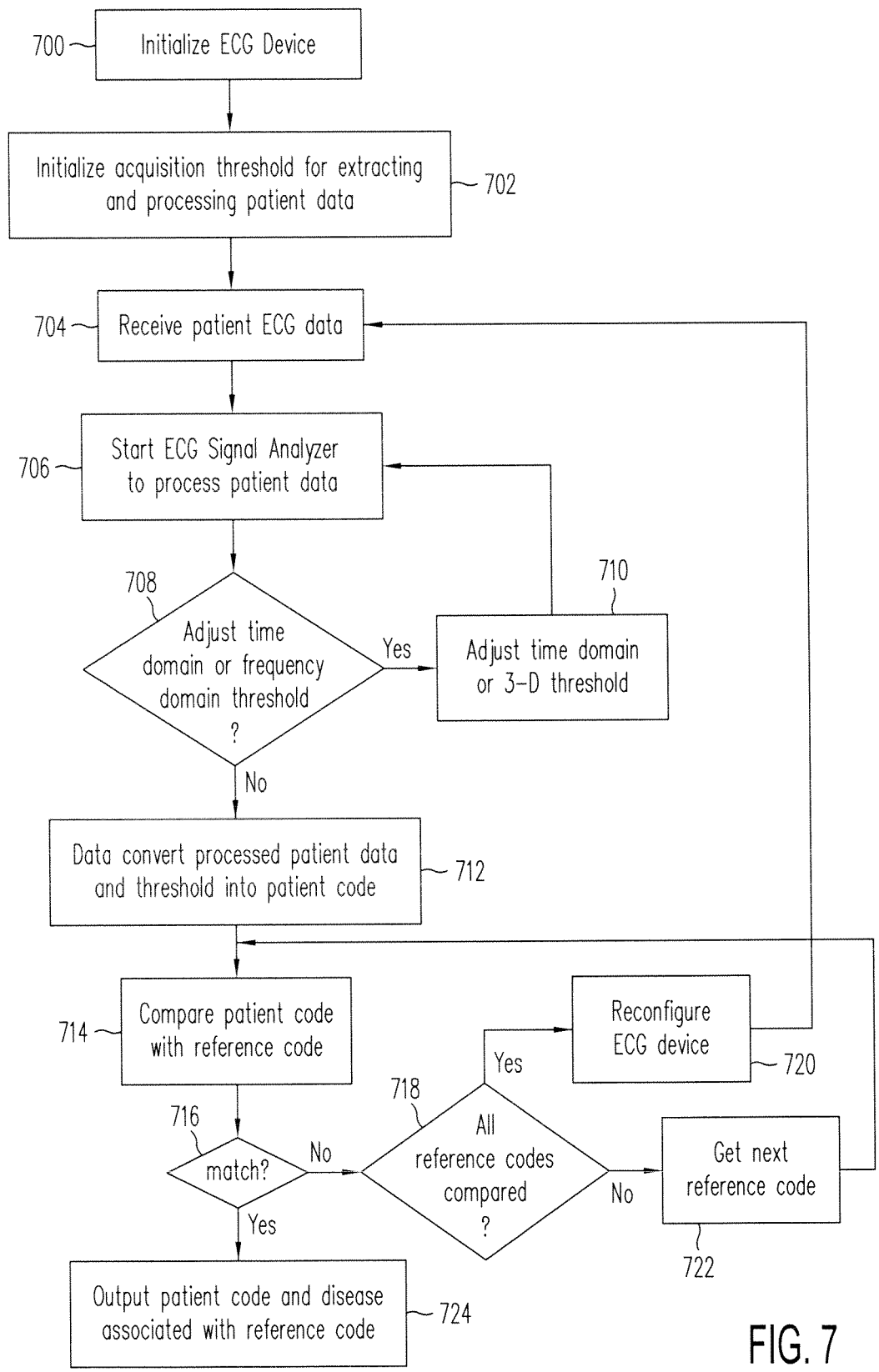
FIG. 7 shows a flow chart of the processing of the patient ECG signals by the dual-track ECG signal analyzer to compare the 2-D and 3-D information of the patient ECG signals with that of the reference database to identify cardiovascular conditions of the patient and to control the ECG device according to one embodiment of the present invention.

FIG. 7 shows a flow chart of the processing of the patient ECG signals by the dual-track ECG signal analyzer to compare the 2-D and 3-D information of the patient ECG signals with that of the reference database to identify cardiovascular conditions of the patient and to control the ECG device according to one embodiment of the present invention. In 700, the process initializes ECG device 100 to use a specified number of channels, a specified sampling duration, a specified sampling mode, and other parameters used to capture the ECG signals of the patient.

In 702, the process initializes the detection threshold used for extracting and processing the patient ECG signals. For example, 702 may initialize the detection threshold to be compared with the peak of the QRS complex in the time domain to identify the QRS complex in the patient ECG signals. In one or more embodiments, 702 may initialize the detection threshold to be compared with the energies in certain frequency bands occupied by the QRS complex in the frequency domain to identify the QRS complex. In one or more embodiments, 702 may initialize other parameters that are used to extract and process the patient ECG signals such as the frequency range, frequency resolution or time resolution, range of time translation, etc., used by the 3-D signal processing of the patient ECG signals.

In 704, the process receives patient ECG data from ECG device 100. In 706, the process starts ECG signal analyzer 104 to process the patient ECG signals. ECG signal analyzer 104 may use wavelet transform to perform 2-D analyses to identify time-domain signal characteristics, and 3-D analyses to identify time-domain and frequency-domain signal information of the patient ECG signal waveforms. ECG signal analyzer 104 may perform a first iteration of the wavelet transform to remove or attenuate noise from the patient ECG signals, reconstruct the noise-filtered patient ECG signals in the time domain, perform a second iteration of the wavelet transform on the reconstructed noise-filtered patient ECG signals, process/extract/analyze the wavelet transform decomposition of the reconstructed patient ECG signals using the detection threshold to identify time domain signal characteristics of the patient ECG signals, and perform 3-D analyses to extract 3-D time-domain and frequency-domain information of the patient ECG signals.

In 708, the process determines if the detection threshold used for extracting and processing the patient ECG signals needs to be adjusted. For example, if the detection threshold in the time domain or in the frequency domain used to identify the QRS complex is set too high such that no QRS complex is detected in the reconstructed patient ECG signals, the detection threshold may have to be adjusted downward. On the other hand, if the detection threshold is set too low such that false QRS complexes are detected, the detection threshold may have to be adjusted upward. In 710, the process adjusts the detection threshold. In 706, the process uses the new detection threshold to re-extract and reprocess the patient ECG signals.

In 712, the process converts the signal characteristics of the patient ECG signals from the time domain analyses and from the 3-D analyses into coded patient data to facilitate the comparison of the signal characteristics of the patient ECG signals with those of the reference ECG signals. In one or more embodiments, the comparison may be performed using un-encoded signal characteristics of the patient ECG signals. The process may also encode the detection threshold for the QRS complex, and other parameters used in the signal extraction and processing steps.

In 714, the process compares the coded or un-encoded patient data with the coded or un-encoded reference data in reference database 112 to determine if there is a sufficient match between the signal characteristics of the ECG signals of the patient and any reference data. The process for the comparison may include correlation, statistical pattern matching, Euclidean distance calculation, and other types of similarity assessment to generate a measure of the match between the values for each encoded or un-encoded field. In one or more embodiments, the process may compare successive 2-D projections of the coded reference data with those of the coded patient data. In one or more embodiments, the process may use a matrix comparison technique to compare the un-encoded data at different levels of details as explained in FIG. 5. The process may compare the coded or un-encoded patient data with a series of coded or un-encoded reference data each of which is representative of a classified cardiovascular condition. In one or more embodiments, the coded or un-encoded reference data representative of a cardiovascular condition may have a range of values that corresponds to a probability that a patient whose coded or un-encoded patient data falls within the specified range would have the cardiovascular condition.

In 716, a match may be declared when the values in the un-encoded fields or in the encoded fields encoding the time domain and/or the 3-D signal characteristics of the patient data fall within the range of values in the un-encoded or encoded fields of a reference data. In one or more embodiments, a match may be declared when a measure of the matching operation exceeds a programmable detection threshold.

In 724, if there is a match, the process may output the coded or un-encoded patient code, the ECG signal waveform of the patient, the matching coded or un-encoded reference data, the reference ECG signal corresponding to the matching coded or un-encoded reference data, the cardiovascular condition corresponding to the matching coded or un-encoded reference code, the probability that the patient has the cardiovascular condition, etc. In one or more embodiments, an image of the heart corresponding to the cardiovascular condition may also be generated and output.

In 718, if there is no match between the coded or un-encoded patient data and the current coded or un-encoded reference data, the process determines if all coded or un-encoded reference data have been compared with the coded or un-encoded patient data. If there are still more coded or un-encoded reference data to be compared, in 722, the process reads the next coded or un-encoded reference data from reference database 112. The process repeats the comparison in 714 until a match is found or until all the coded or un-encoded reference data have been compared. If all the coded or un-encoded reference data are compared without finding a match, in 720, the process reconfigures ECG device 100 to resample the patient ECG signals. For example, the process may change the number of channels, the sampling duration, the sampling mode, or other parameters of ECG device 100. The process may also reinitialize the detection threshold or other parameters used for extracting and processing the patient ECG signals without reconfiguring ECG device 100. In one or more embodiments, the process may reconfigure ECG 100 as well as reinitialize the parameters used for extracting and processing the patient ECG signals. The process repeats 704 to resample patient ECG signals from ECG device 100 if ECG device 100 has been reconfigured, or repeats 706 to use wavelet transform to reprocess and re-extract 2-D and 3-D signal characteristics of the patient ECG signals. The process may continue until a match is found or until the end of a time out period.

Figure 8:
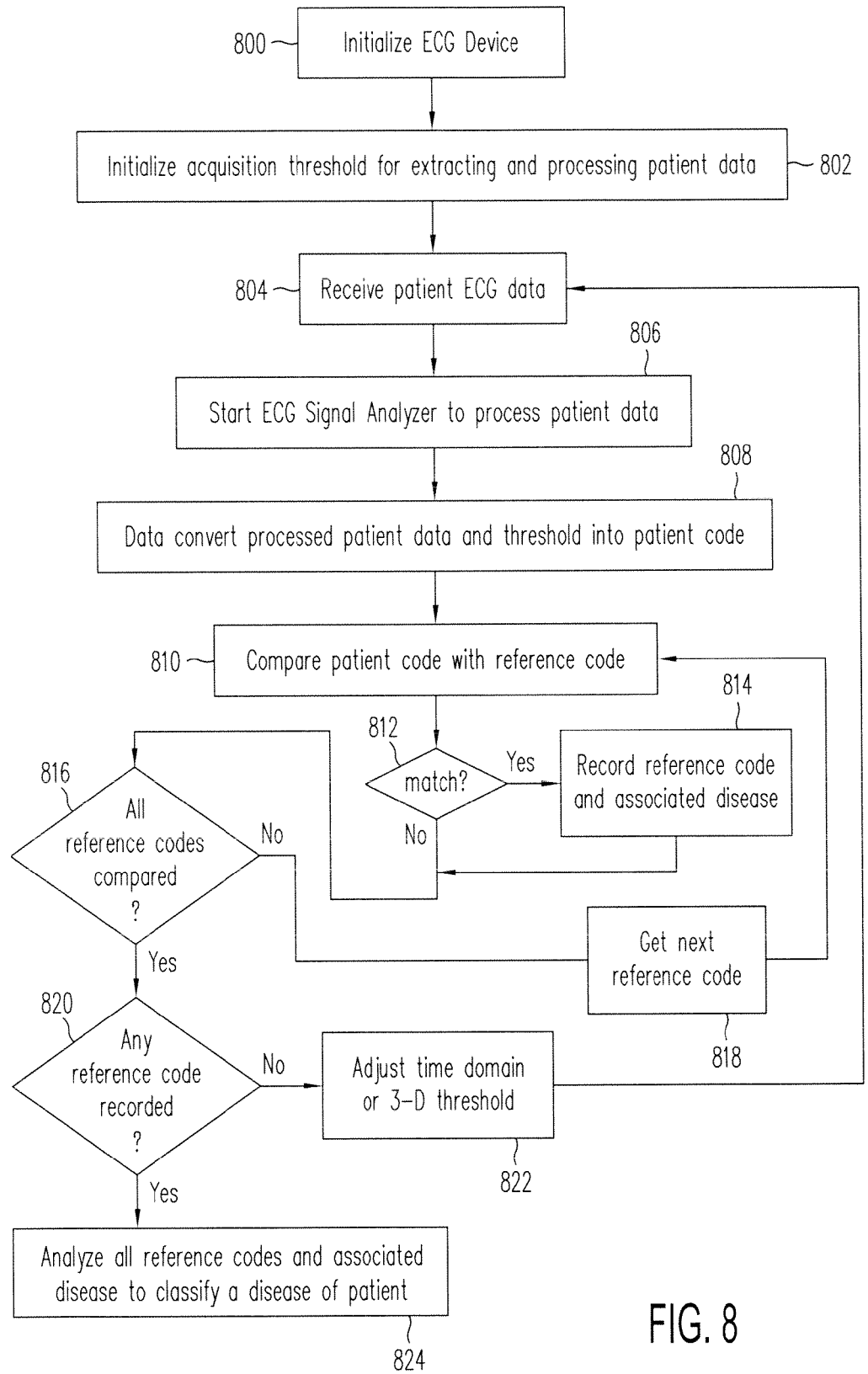
FIG. 8 shows a flow chart of the processing of the patient ECG signals by the dual-track ECG signal analyzer to compare the 2-D and 3-D information of the patient ECG signals with that of the reference database to identify cardiovascular conditions of the patient and to control the ECG device according to another embodiment of the present invention.

FIG. 8 shows a flow chart of the processing of the patient ECG signals by the dual-track ECG signal analyzer to compare the 2-D and 3-D information of the patient ECG signals with that of the reference database to identify cardiovascular conditions of the patient and to control the ECG device according to another embodiment of the present invention. Processing step 800 to initialize ECG device 100, 802 to initialize detection threshold for extracting and processing patient ECG signals. 804 to receive patient ECG signals, 806 to start ECG signal analyzer 104 to process and extract patient ECG signals, and 808 to convert the signal characteristics of the patient ECG signals into coded patient data are the same as 700, 702, 704, 706, and 712 of FIG. 7, respectively. A detail description of these modules will not be repeated for the sake of brevity.

In 810, similar to step 714 of FIG. 7, the process compares the coded or un-encoded patient data with the coded or un-encoded reference data in reference database 112 to determine if there is a sufficient match between the signal characteristics of the ECG signals of the patient and the reference data. However, in contrast to FIG. 7 where the comparison stops when a matching coded or un-encoded reference data is found, the coded or un-encoded patient data here is compared with all the coded or un-encoded reference in reference database 112. When there are multiple matching coded or un-encoded reference data, they may be sorted to find the coded or un-encoded reference data with the best match. For example, the coded or un-encoded reference data that has the highest score or the best measure of the similarity between the values of the encoded or un-encoded fields may be declared as the best match. In one or more embodiments, if the coded or un-encoded reference data representative of a cardiovascular condition has a range of values corresponding to a probability that a patient whose coded or un-encoded data falls within the specified range would have the cardiovascular condition, the best matching coded or un-encoded reference data may be the one with the highest probability of a corresponding cardiovascular condition.

In 812, as in 716 of FIG. 4, a match may be declared when the values in the un-encoded fields or in the encoded fields encoding the time domain and/or the 3-D signal characteristics of the patient data fall within the range of values in the un-encoded or encoded fields of a reference data. In one or more embodiments, a match may be declared when a measure of the matching operation exceeds a programmable detection threshold.

In 814, if there is a match, the process may record the matching coded or un-encoded reference data, the reference ECG signal corresponding to the coded or un-encoded reference data, the cardiovascular condition corresponding to the coded or un-encodedd reference code, the probability that the patient has the cardiovascular condition, etc., in reference database 112 or in other memories such as memories used by controller 118. The process continues to 816. If there is no match in 812, the process also continues to 816.

In 816, the process determines if all coded or un-encoded reference data have been compared with the coded or un-encoded patient data. If there are still more coded or un-encoded reference data to be compared, in 818, the process reads the next coded or un-encoded reference data from reference database 112. The process repeats the comparison in 810 until all the coded or un-encoded reference data have been compared. If all the coded or un-encoded reference data have been compared, in 820, the process determines if at least one matching coded or un-encoded reference data has been found by checking to see if any coded reference data has been recorded. If there has not been a match, in 822, the process reconfigures ECG device 100 to resample the patient ECG signals, and/or reinitializes the detection threshold or other parameters used for extracting and processing the patient ECG signals, similar to 720 in FIG. 7. The process repeats 804 to resample patient ECG signals from ECG device 100 if ECG device 100 has been reconfigured, or repeats 806 at to use wavelet transform to reprocess and re-extract 2-D and 3-D signal characteristics of the patient ECG signals. The process may continue until all coded or un-encoded reference data have been compared with the coded or un-encoded patient data or until the end of a time out period.

In 824, if at least one matching coded or un-encoded reference data has been found, the process may find the best match if there are multiple matches. As discussed, the best match may be the coded or un-encoded reference data that has the highest score or the best measure of the similarity between the values of the encoded or un-encoded fields. In one or more embodiments, the best match may be the coded or un-encoded reference data with the highest probability of a corresponding cardiovascular condition. The process may output the coded or un-encoded patient code, the ECG signal waveform of the patient, the best matching coded or un-encoded reference data, the reference ECG signal corresponding to the best matching coded or un-encoded reference data, the cardiovascular condition corresponding to the best matching coded or un-encoded reference code, the probability that the patient has the cardiovascular condition, etc. In one or more embodiments, an image of the heart corresponding to the cardiovascular condition may also be generated and output.

The descriptions set forth above are provided to illustrate one or more embodiments of the present invention and are not intended to limit the scope of the present invention. Although the invention is described in details with reference to the embodiments, a person skilled in the art may obtain other embodiments of the invention through modification of the disclosed embodiment or replacement of equivalent parts. For example, while the embodiments are described as using wavelet transform of ECG signals to identify cardiovascular conditions, other types of medical diagnostic signals such as electromyography (EMG), or imaging signals such as computerized axial tomography (CAT) scan, magnetic resonance imaging (MRI), etc., may be processed and analyzed using wavelet transform as described to identify neural, muscular-skeletal, brain, or other types of medical conditions. It is understood that any modification, replacement of equivalent parts and improvement are within the scope of the present invention and do not depart from the spirit and principle of the invention as hereinafter claimed.

What is claimed is:

1. A method for identifying a medical condition using electrocardiogram (ECG) signals by a processor, comprising the processor:
   receiving a plurality of reference ECG signals from a reference data source, wherein each of the plurality of reference ECG signals comprises a plurality of QRS complexes;
   running a first iteration of wavelet transform on the plurality of reference ECG signals to remove noise from the plurality of reference ECG signals;
   running a second iteration of wavelet transform on the plurality of reference ECG signals with the noise removed to generate a plurality of wavelet transform decomposition of reconstructed reference ECG signals;
   receiving ECG signals of a patient from an ECG machine, wherein the ECG signals of the patient are acquired using a set of parameters of the ECG machine, and wherein the ECG signals of the patient comprise a plurality of QRS complexes;
   running a first iteration of wavelet transform on the ECG signals of the patient to remove noise from the ECG signals of the patient;
   running a second iteration of wavelet transform on the ECG signals of the patient with the noise removed to generate wavelet transform decomposition of reconstructed patient ECG signals;
   analyzing energy distribution in time domain and frequency domain of the plurality of wavelet transform decomposition of reconstructed reference ECG signals to generate signal characteristics of the plurality of QRS complexes of the plurality of reference ECG signals;
   encoding the signal characteristics of the plurality of QRS complexes of the plurality of reference ECG signals to generate a plurality of coded reference data;
   analyzing energy distribution in the time domain and frequency domain of the wavelet transform decomposition of reconstructed patient ECG signals to generate signal characteristics of the plurality of QRS complexes of the ECG signals of the patient;
   encoding the signal characteristics of the plurality of QRS complexes of the ECG signals of the patient to generate coded patient data;
   comparing the coded patient data with the plurality of coded reference data to generate a best match between the signal characteristics of the plurality of QRS complexes of the ECG signals of the patient and one or more of the signal characteristics of the plurality of QRS complexes of the plurality of reference ECG signals to assist in identifying the medical condition of the patient; and
   configuring the ECG machine to adjust the set of parameters to acquire additional ECG signals of the patient in response to results of said comparing.

2. The method of claim 1,
   wherein said running a second iteration of wavelet transform on the plurality of reference ECG signals with the noise removed to generate the plurality of wavelet transform decomposition of reconstructed reference ECG signals comprises:
     reconstructing the plurality of reference ECG signals with the noise removed to generate a plurality of reconstructed reference ECG signals; and
     running the second iteration of wavelet transform on the plurality of reconstructed reference ECG signals to generate the plurality of the wavelet transform decomposition of reconstructed reference ECG signals in the time domain and in the frequency domain, and
   wherein said running a second iteration of wavelet transform on the ECG signals of the patient with the noise removed to generate the wavelet transform decomposition of reconstructed patient ECG signals comprises:
     reconstructing the ECG signals of the patient with the noise removed to generate reconstructed ECG signals of the patient; and
     running the second iteration of wavelet transform on the reconstructed ECG signals of the patient to generate the wavelet transform decomposition of reconstructed patient ECG signals in the time domain and in the frequency domain.

3. The method of claim 2,
wherein the signal characteristics of the plurality of QRS complexes of the plurality of reference ECG signals comprises the signal characteristics in time domain and in 3-D time and frequency domains,
wherein said analyzing energy distribution in the time domain and frequency domain of the plurality of wavelet transform decomposition of reconstructed reference ECG signals to generate signal characteristics of the plurality of QRS complexes of the plurality of reference ECG signals comprises:
  extracting and analyzing the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the time domain; and
  extracting and analyzing the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the 3-D time and frequency domains,
wherein the signal characteristics of the plurality of QRS complexes of the ECG signals of the patient comprise signal characteristics in time domain and in 3-D time and frequency domains, and
wherein said analyzing energy distribution in the time domain and frequency domain of the wavelet transform decomposition of reconstructed patient ECG signals to generate the signal characteristics of the plurality of QRS complexes of the ECG signals of the patient comprises:
  extracting and analyzing the energy distribution of the wavelet transform decomposition of the reconstructed patient ECG signals in the time domain and in the frequency domain to generate the signal characteristics of the Plurality of QRS complexes of the reconstructed patient ECG signals in the time domain; and
  extracting and analyzing the energy distribution of the wavelet transform decomposition of the reconstructed patient ECG signals in the time domain and in the frequency domain to generate the signal characteristics of the plurality of QRS complexes of the reconstructed patient ECG signals in the 3-D time and frequency domains.

4. The method of claim 3,
wherein the plurality of coded reference data comprises:
  a plurality of time encoded reference data encoding the signal characteristics of the plurality of QRS complexes of the plurality of reconstructed reference ECG signals in time domain; and
  a plurality of time-and-frequency encoded reference data encoding the signal characteristics of the plurality of QRS complexes of the plurality of reconstructed reference ECG signals in 3-0 time and frequency domains,
wherein the coded patient data comprises:
  time encoded patient data encoding the signal characteristics of the plurality of QRS complexes of the reconstructed patient signals in time domain; and
  time-and-frequency encoded patient data encoding the signal characteristics of the plurality of QRS complexes of the reconstructed patient signals in 3-D time and frequency domains,
and wherein said comparing the coded patient data with the plurality of coded reference data comprises:
  comparing the time encoded patient data with the plurality of time encoded reference data; and
  comparing the time-and-frequency encoded patient data with the plurality of time-and-frequency encoded reference data to find the best match.

5. The method of claim 1, wherein the signal characteristics of the plurality of QRS complexes of the plurality of reference ECG signals that best match the signal characteristics of the plurality of QRS complexes of the ECG signals of the patient are associated with a diagnosed medical condition and the patient is identified as having the diagnosed medical condition.

6. The method of claim 1, further comprising using results of said comparing the coded patient data with the plurality of coded reference data to adjust parameters used for said analyzing energy distribution in the time domain and frequency domain of the wavelet transform decomposition of reconstructed patient ECG to generate signal characteristics of the plurality of QRS complexes of the ECG signals of the patient.

7. The method of claim 1, further comprising using results of said comparing the coded patient data with the plurality of coded reference data to adjust parameters used for said analyzing energy distribution in the time domain and frequency domain of the plurality of wavelet transform decomposition of reconstructed reference ECG signals to generate signal characteristics of the plurality of QRS complexes of the plurality of reference ECG signals.

8. The method of claim 1, further comprising classifying the plurality of coded reference data to identify the coded reference data that are associated with one or more diagnosed medical conditions when the plurality of reference ECG signals received from the reference data source corresponding to the coded reference data is associated with the one or more diagnosed medical conditions.

9. The method of claim 8, wherein said comparing the coded patient data with the plurality of coded reference data comprises comparing the coded patient data with the coded reference data that are identified as associated with a plurality of the diagnosed medical conditions.

10. The method of claim 1, wherein the plurality of the diagnosed medical conditions is a plurality of cardiovascular conditions.

11. The method of claim 1, wherein said comparing the coded patient data with the plurality of coded reference data comprises comparing from a coarse resolution in time or frequency to successively finer resolution in time or frequency using a matrix comparison.

12. A system comprising:
  a dual-track wavelet transform module adapted to:
    receive a plurality of reference electrocardiogram (ECG) signals from a reference data source, wherein each dual-track wavelet transform module of the plurality of reference ECG signals comprises a plurality of QRS complexes;
    run a first iteration of wavelet transform on the plurality of reference ECG signals to remove noise from the plurality of reference ECG signals;
    run a second iteration of wavelet transform on the plurality of reference ECG signals with the noise removed to generate a plurality of wavelet transform decomposition of reconstructed reference ECG signals;

receive ECG signals of a patient from an ECG machine, wherein the ECG signals of the patient are acquired using a set of parameters of the ECG machine, and wherein the ECG signals of the patient comprises a plurality of QRS complexes;

run a first iteration of wavelet transform on the ECG signals of the patient to remove noise from the ECG signals of the patient; and run a second iteration of wavelet transform on the ECG signals of the patient with the noise removed to generate wavelet transform decomposition of reconstructed patient ECG signals, a signal processor module adapted to:

analyze energy distribution in time domain and frequency domain of the plurality of wavelet transform decomposition of reconstructed reference ECG signals to generate signal characteristics of the plurality of QRS complexes of the plurality of reference ECG signals;

encode the signal characteristics of the plurality of QRS complexes of the plurality of reference ECG signals to generate a plurality of coded reference data;

analyze energy distribution in the time domain and frequency domain of the wavelet transform decomposition of reconstructed patient ECG signals to generate signal characteristics of the plurality of QRS complexes of the ECG signals of the patient;

encode the signal characteristics of the plurality of QRS complexes of the ECG signals of the patient to generate coded patient data, and a comparison module adapted to:

compare the coded patient data with the plurality of coded reference data to identify a best match between the signal characteristics of the plurality of QRS complexes of the ECG signals of the patient and one or more of the signal characteristics of the plurality of QRS complexes of the plurality of reference ECG signals as an aid to identify a medical condition of the patient; and configure the ECG machine to adjust the set of parameters to acquire additional ECG signals of the patient in response to results of the compare of the coded patient data with the plurality of coded reference data.

13. The system of claim 12, wherein the dual-track wavelet transform module is further adapted to:

reconstruct the plurality of reference ECG signals with the noise removed to generate a plurality of reconstructed reference ECG signals;

run the second iteration of wavelet transform on the plurality of reconstructed reference ECG signals to generate the plurality of the wavelet transform decomposition of reconstructed reference ECG signals in the time domain and in the frequency domain;

reconstruct the ECG signals of the patient with the noise removed to generate reconstructed ECG signals of the patient; and run the second iteration of wavelet transform on the reconstructed ECG signals of the patient to generate the wavelet transform decomposition of reconstructed patient ECG signals in the time domain and in the frequency domain.

14. The system of claim 13, wherein the signal characteristics of the plurality of QRS complexes of the plurality of reference ECG signals comprise the signal characteristics in time domain and in 3-D time and frequency domains, wherein the signal processor module is further adapted to:

extract and analyze the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the time domain; and extract and analyze the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the 3-D time and frequency domains, wherein the signal characteristics of the plurality of QRS complexes of the ECG signals of the patient comprise signal characteristics in time domain and in 3-D time and frequency domains, and wherein the signal processor module is further adapted to:

extract and analyze the energy distribution of the wavelet transform decomposition of the reconstructed patient ECG signals in the time domain and in the frequency domain to generate the signal characteristics of the plurality of QRS complexes of the patient ECG signals in the time domain; and extract and analyze the energy distribution of the wavelet transform decomposition of the reconstructed patient ECG signals in the time domain and in the frequency domain to generate the signal characteristics of the plurality of QRS complexes of the patient ECG signals in the 3-D time and frequency domains.

15. The system of claim 14, wherein the plurality of coded reference data comprises:

a plurality of time encoded reference data encoding the signal characteristics of the plurality of QRS complexes of the plurality of reconstructed reference ECG signals in time domain; and a plurality of time-and-frequency encoded reference data encoding the signal characteristics of the plurality of QRS complexes of the plurality of reconstructed reference ECG signals in 3-D time and frequency domains, wherein the coded patient data comprises:

time encoded patient data encoding the signal characteristics of the plurality of QRS complexes of the reconstructed patient signals in time domain; and time-and-frequency encoded patient data encoding the signal characteristics of the plurality of QRS complexes of the reconstructed patient signals in 3-D time and frequency domains, and wherein the comparison module is further adapted to:

compare the time encoded patient data with the plurality of time encoded reference data; and compare the time-and-frequency encoded patient data with the plurality of time-and-frequency encoded reference data to find the best match.

16. The system of claim 12, wherein the signal characteristics of the plurality of QRS complexes of the plurality of reference ECG signals that best match the signal characteristics of the plurality of QRS complexes of the ECG signals of the patient are associated with a diagnosed medical condition and the patient is identified as having the diagnosed medical condition.

17. The system of claim 12, wherein the comparison module is further adapted to compare the coded patient data with the plurality of coded reference data to adjust parameters used by the signal processor module to analyze the energy distribution in the time domain and frequency domain of the wavelet transform decomposition of reconstructed patient ECG to generate signal characteristics of the plurality of QRS complexes of the ECG signals of the patient.

18. The system of claim 12, wherein the comparison module is further adapted to compare the coded patient data with the plurality of coded reference data to adjust parameters used by the signal processor module to analyze the energy distribution in the time domain and frequency domain of the plurality of wavelet transform decomposition of reconstructed reference ECG signals to generate signal characteristics of the plurality of QRS complexes of the plurality of reference ECG signals.

19. The system of claim 12, wherein the signal processor module is further adapted to classify the plurality of coded reference data to identify the coded reference data that are associated with one or more diagnosed medical conditions when the plurality of reference ECG signals received from the reference data source corresponding to the coded reference data are associated with the one or more diagnosed medical conditions.

20. The system of claim 19, wherein the comparison module is further adapted to compare the coded patient data with the coded reference data that are identified as associated with a plurality of the one or more diagnosed medical conditions.

21. The system of claim 12, wherein the plurality of the diagnosed medical conditions is a plurality of cardiovascular conditions.

22. The system of claim 12, wherein the comparison module is further adapted to compare the coded patient data with the plurality of coded reference data from a coarse resolution in time or frequency to successively finer resolution in time or frequency using a matrix comparison.

23. A non-transitory computer readable medium comprising:
a reference database that stores signal characteristics of a plurality of QRS complexes of a plurality of reference electrocardiogram (ECG) signals to be compared with signal characteristics of a plurality of QRS complexes of ECG signals of a patient to help in identifying a medical condition of the patient, wherein the signal characteristics of the plurality of QRS complexes of the plurality of reference ECG signals are generated by a process that:
uses a first iteration of wavelet transform to transform a plurality of reference ECG signals received from a reference data source to remove noise from the plurality of reference ECG signals;
uses a second iteration of wavelet transform on the plurality of reference ECG signals with the noise removed to generate a plurality of wavelet transform decomposition of reconstructed reference ECG signals; and analyzes energy distribution in time domain and frequency domain of the plurality of wavelet transform decomposition of reconstructed reference ECG signals to generate the signal characteristics of the plurality of QRS complexes of the plurality of reference ECG signals.

24. The non-transitory computer readable medium of claim 23, wherein the process that uses a second iteration of wavelet transform on the plurality of reference ECG signals with the noise removed to generate the plurality of wavelet transform decomposition of reconstructed reference ECG signals comprises:
reconstructs the plurality of reference ECG signals with the noise removed to generate a plurality of reconstructed reference ECG signals;
runs the second iteration of wavelet transform on the plurality of reconstructed reference ECG signals to generate the plurality of the wavelet transform decomposition of reconstructed reference ECG signals in the time domain and in the frequency domain.

25. The non-transitory computer readable medium of claim 24, wherein the signal characteristics of the plurality of QRS complexes of the plurality of reference ECG signals comprise the signal characteristics in time domain and in 3-D time and frequency domains, and wherein the process that analyzes energy distribution in the time domain and frequency domain of the plurality of wavelet transform decomposition of reconstructed reference ECG signals to generate the signal characteristics of the plurality of QRS complexes of the plurality of reference ECG signals:
extracts and analyzes the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the time domain; and
extracts and analyzes the energy distribution of the plurality of wavelet transform decomposition of reconstructed reference ECG signals in the time domain and in the frequency domain to generate the signal characteristics of the plurality of QRS complexes of the plurality of reconstructed reference ECG signals in the 3-D time and frequency domains.

26. The non-transitory computer readable medium of claim 23, wherein the signal characteristics of the plurality of QRS complexes of the plurality of reference ECG signals are encoded to generate a plurality of coded reference data to be compared with signal characteristics of a plurality of QRS complexes of ECG signals of the patient that are encoded, and
wherein the reference database further comprises classified coded reference data that are associated with a medical condition, wherein the classified coded reference data are identified from the signal characteristics of a plurality of QRS complexes of a plurality of reference ECG signals associated with the medical condition.

* * * * *

UNITED STATES PATENT AND TRADEMARK OFFICE
CERTIFICATE OF CORRECTION

PATENT NO. : 9,642,577 B1
APPLICATION NO. : 15/237913
DATED : May 9, 2017
INVENTOR(S) : Fu Yu Li et al.

It is certified that error appears in the above-identified patent and that said Letters Patent is hereby corrected as shown below:

In the Claims

Column 21, Line 42, "Plurality" should be --plurality--

Column 21, Line 61, "3-0" should be --3-D--

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*